United States Patent
Hara et al.

(10) Patent No.: US 9,190,992 B2
(45) Date of Patent: Nov. 17, 2015

(54) SEMICONDUCTOR DEVICE AND ULTRASONIC DIAGNOSTIC APPARATUS USING THE SAME

(75) Inventors: Kenji Hara, Hitachinaka (JP); Junichi Sakano, Hitachi (JP)

(73) Assignee: Hitachi Power Semiconductor Device, Ltd., Hitachi-shi (JP)

( * ) Notice: Subject to any disclaimer, the term of this patent is extended or adjusted under 35 U.S.C. 154(b) by 1043 days.

(21) Appl. No.: 13/282,882

(22) Filed: Oct. 27, 2011

(65) Prior Publication Data

US 2012/0108963 A1    May 3, 2012

(30) Foreign Application Priority Data

Oct. 28, 2010   (JP) .................. 2010-241711

(51) Int. Cl.
*H03K 17/687* (2006.01)
*H03K 17/06* (2006.01)
*H03K 17/081* (2006.01)
*H03K 17/10* (2006.01)

(52) U.S. Cl.
CPC ........ *H03K 17/063* (2013.01); *H03K 17/08104* (2013.01); *H03K 17/102* (2013.01); *H03K 17/6874* (2013.01)

(58) Field of Classification Search
CPC ............. H03K 17/063; H03K 19/018521; H03K 17/08122–17/08142
See application file for complete search history.

(56) References Cited

U.S. PATENT DOCUMENTS 6,509,781 B2 * 1/2003 Dufort ......................... 327/434
6,617,906 B1   9/2003 Hastings 2002/0135415 A1   9/2002 Dufort
2006/0017391 A1   1/2006 Hasegawa
2006/0077000 A1   4/2006 Goudo
2006/0169909 A1 * 8/2006 Oka .............................. 250/372

(Continued)

FOREIGN PATENT DOCUMENTS

CN   1459145 A   11/2003
CN   1725640 A   1/2006

(Continued)

OTHER PUBLICATIONS

Chinese Office Action dated Feb. 7, 2014, with English Translation (eighteen (18) pages).

(Continued)

*Primary Examiner* — Sibin Chen
(74) *Attorney, Agent, or Firm* — Crowell & Moring LLP (57) ABSTRACT

The present invention provides a semiconductor device of a bi-directional analog switch having a high linearity and a low electric power loss. An ultrasonic diagnostic apparatus having a high degree of detection accuracy, comprising the semiconductor device, is also provided. A semiconductor device of a bi-directional analog switch, comprising a switch circuit capable of switching ON or OFF bi-directionally, and built-in driving circuits for the switch circuit, wherein the driving circuit is connected to first and second power supplies, and a first power supply voltage is higher than a maximum voltage of a signal applied to an input/output terminal of the switch circuit, a second power supply voltage is lower than a minimum voltage of a signal applied to an input/output terminal of the switch circuit, and the driving circuit comprises a Zener diode and a p-type MOSFET connected in series between the first power supply and the switch circuit.

6 Claims, 7 Drawing Sheets

(56) References Cited

U.S. PATENT DOCUMENTS

| | | |
|---|---|---|
| 2007/0063747 A1 | 3/2007 | Ota et al. |
| 2007/0159751 A1* | 7/2007 | Hussein et al. ............... 361/100 |
| 2011/0028845 A1* | 2/2011 | Haider et al. ............... 600/459 |

FOREIGN PATENT DOCUMENTS

| | | | |
|---|---|---|---|
| JP | 2004-531929 A | 10/2004 | |
| JP | 2006-033723 A | 2/2006 | |
| JP | 2007-116653 A | 5/2007 | |
| JP | 2009-111304 A | 5/2009 | |
| JP | 2010-530616 A | 9/2010 | |
| WO | WO 2008/156674 A1 | 12/2008 | |

OTHER PUBLICATIONS

Notice of Reasons for Rejection with English translation dated Oct. 22, 2013 (six (6) pages).

European Search Report dated Feb. 13, 2012 (seven (7) pages).

\* cited by examiner

SEMICONDUCTOR DEVICE AND ULTRASONIC DIAGNOSTIC APPARATUS USING THE SAME

CROSS REFERENCE TO RELATED APPLICATIONS

The present patent application claims the benefit under 35 U.S.C. 119 of Japanese Patent Application No. 2010-241711 filed on Oct. 28, 2010, the disclosure of which is incorporated into this patent application by reference.

BACKGROUND OF THE INVENTION

1. Field of the Invention

The present invention relates to a semiconductor device configuring a high-voltage bi-directional analog switch and an ultrasonic apparatus using the same.

2. Description of the Related Art

High-voltage bi-directional analog switches (hereinafter referred to as "switch", as required) are utilized to allocate signals to a plurality of oscillators equipped in probes, for example, in a field of ultrasonic diagnostic apparatus. When a bi-directional analog switch is utilized for switching signals of the ultrasonic diagnostic apparatus, a high linearity within an operational range is required for the bi-directional analog switch, so as to suppress a signal distortion affecting a picture quality of diagnostic images.

Moreover, JP 2004-531929 A discloses a technique which improves a linearity of the bi-directional analog switch.

SUMMARY OF THE INVENTION

However, conventional bi-directional analog switches have not always secured linearities which are sufficiently good. Moreover, in the case of a circuit configuration disclosed in JP 2004-531929 A, there has been a problem of a significant electric power loss, since some control signal lines have paths to continue flowing the electric current, in either case of a switch-ON state or a switch-OFF state.

Therefore, the present invention is to solve the aforementioned problem, and an object of the present invention is to provide a semiconductor device of the bi-directional analog switch which has a high linearity and a low electric power loss.

In addition, another object of the present invention is to provide an ultrasonic diagnostic apparatus, utilizing the aforementioned semiconductor device and having a high degree of detection accuracy.

In order to solve the aforementioned problem and to achieve the object of the present invention, an apparatus configuration of the present invention has been made as mentioned below.

That is to say, the apparatus is a semiconductor device comprising a switch circuit capable of switching ON or switching OFF, bi-directionally and a driving circuit for driving the switch circuit therein, wherein the driving circuit is connected to a first power supply and a second power supply, a voltage of the first power supply is equal to or higher than a maximum voltage of a signal applied to input/output terminals of the switch circuit, a voltage of the second power supply is equal to or lower than a minimum voltage of a signal applied to input/output terminals of the switch circuit, and moreover, the driving circuit comprises a Zener diode and a p-type MOSFET connected in series between the first power supply and the switch circuit.

Furthermore, the apparatus is a semiconductor device comprising a switch circuit for enabling switch-ON or switch-OFF in a bi-directional manner and a driving circuit for driving the switch circuit therein, wherein the driving circuit is connected to the first power supply and the second power supply, the voltage of the first power supply is equal to or higher than the maximum voltage of a signal applied to input/output terminals of the switch circuit, the voltage of the second power supply is equal to or lower than the minimum voltage of the signal applied to input/output terminals of the switch circuit, and moreover, the driving circuit comprises a p-type IGBT connected between the first power supply and the switch circuit.

In addition, the semiconductor device is utilized for a switch of a wave-transmission of an ultrasonic signal to an oscillator, for separation-switching a wave-transmission pulse generator and a reception amplifier of the ultrasonic signal, or for switching a probe.

According to the above mentioned configuration, the signal voltage for controlling the switch circuit is secured to be higher than a voltage of a signal to input to the input/output terminal of the switch circuit. Therefore, a semiconductor device of a bi-directional analog switch is realized to secure both of a linearity required for the bi-directional analog switch and a low electric power loss.

Furthermore, according to the above mentioned structure, the ultrasonic diagnostic apparatus has a high degree of detection accuracy, since the apparatus comprises the bi-directional analog switch with characteristics of the high linearity and of a low electric power loss.

As above mentioned, according to the present invention, a semiconductor device of the bi-directional analog switch, having the high linearity and the low electric power loss, can be provided.

Furthermore, an ultrasonic diagnostic apparatus utilizing the semiconductor device and having a high degree of detection accuracy, can be provided.

DETAILED DESCRIPTION OF THE EMBODIMENTS

First Embodiment

Semiconductor Device

Figure 1:
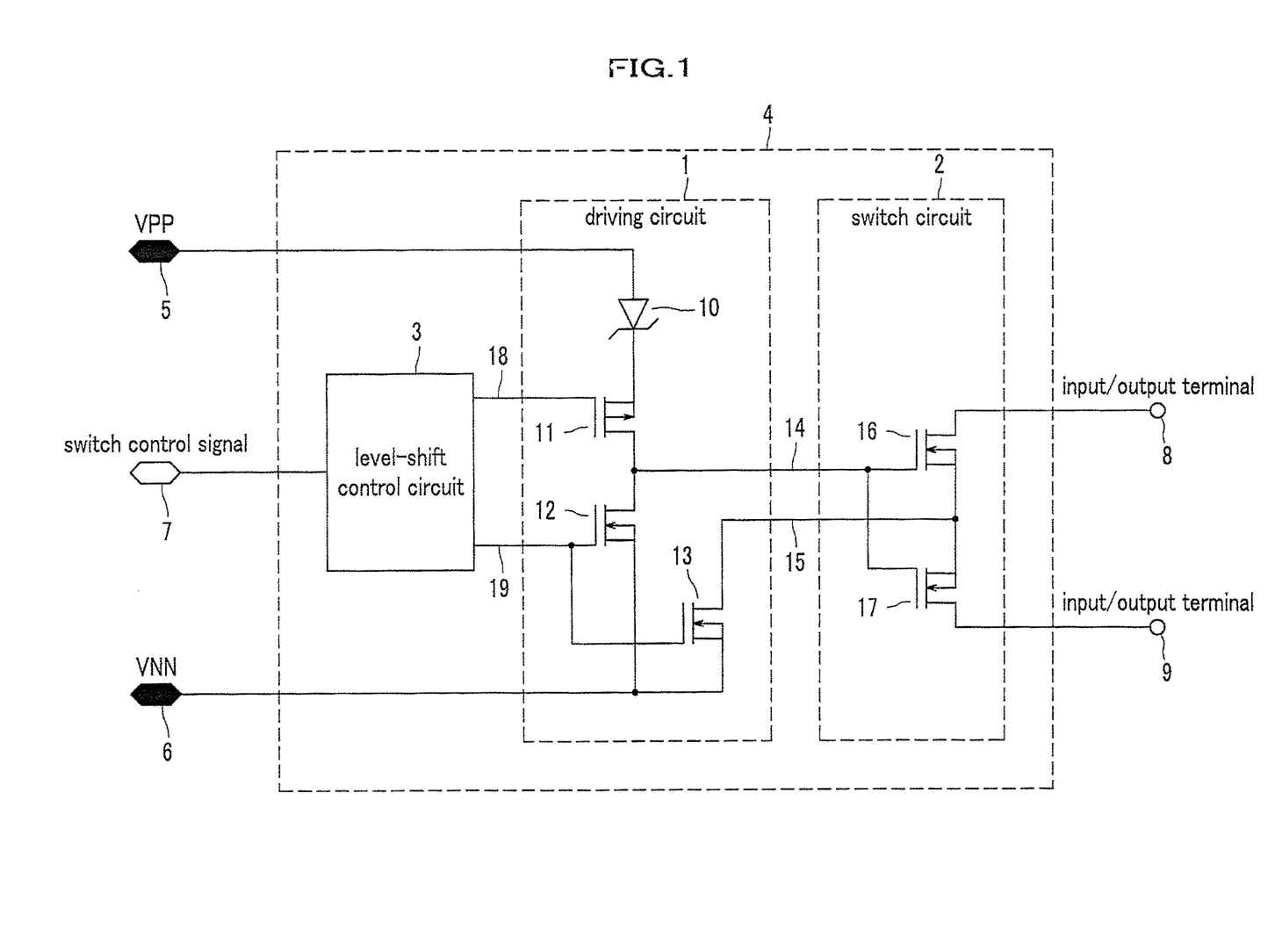
FIG. 1 is a circuit diagram showing a configuration of a semiconductor device according to a first embodiment of the present invention.

A first embodiment of the present invention is described below in detail with reference to the accompanying drawings. FIG. 1 is a circuit diagram showing a configuration according to a first embodiment of the present invention.

In FIG. 1, a semiconductor device in the first embodiment consists of a bi-directional analog switch overall circuit 4.

<<Configuration of Bi-directional Analog Switch Overall Circuit 4>>

The bi-directional analog switch overall circuit 4 is configured, comprising a driving circuit 1, a switch circuit 2, and a level-shift control circuit 3. Moreover, the bi-directional analog switch overall circuit 4 is connected to a high-voltage positive power supply 5 (VPP, a first power supply), a high-voltage negative power supply 6 (VNN, a second power supply), and a switch control signal input terminal 7, and comprises input/output terminals 8 and 9 to be connected to the bi-directional analog switch in the switch circuit 2.

<<Switch Circuit 2<<

The switch circuit 2 is configured, comprising n-type MOSFETs (Metal-Oxide-Semiconductor Field-Effect Transistor) 16 and 17. The n-type MOSFETs 16 and 17 are connected at source terminals and at gate terminals thereof, each other. Incidentally, in the case of MOSFET, a relation between the source and the drain varies depending on a flow direction of an electric current. According to FIG. 1 of the n-type MOSFETs 16 and 17, a terminal having a same electrical potential as a bulk is referred to as a source terminal (source) and a terminal not connecting to the bulk is referred to as a drain terminal (drain).

Thus, the drain terminal of the n-type MOSFET 16 is the input/output terminal 8 for the switch circuit 2 and the drain terminal of the n-type MOSFET 17 is the input/output terminal 9 for the switch circuit 2.

The gate terminals (gate) connected each other to the n-type MOSFETs 16 and 17 are connected to a first output line 14 of the driving circuit 1.

Meanwhile, the source terminals (source) connected each other to the n-type MOSFETs 16 and 17 are connected to a second output line 15 of the driving circuit 1.

The first output line 14 and the second output line 15 of the driving circuit 1 are controlled by a switch control signal 7, which is disposed at an upstream side of the circuit. That is to say, a change of the switch control signal 7 results in an operation of the level-shift control circuit 3. Thereafter, the driving circuit 1 operates on the basis of the control signal given by the first level-shift control circuit output terminal 18 and the second level-shift control circuit output terminal 19 of the level-shift control circuit 3 and switches the switch circuit 2 into a switch-ON state (on, conduction, low impedance) or a switch-OFF state (off, shut down, high impedance). Thus, a signal applied to the input/output terminal (e.g. input/output terminal 8) is propagated (transmitted) to a counterpart input/output terminal (e.g. input/output terminal 9), or is shut down.

Furthermore, the output signals of the driving circuit 1 are described as a first output line 14 and a second output line 15, instead of a first output signal and a second output signal. This is because each of electrical potentials of the first output line 14 and the second output line 15, may be occasionally determined by a factor other than an output driven by the p-type MOSFET 11 and the n-type MOSFET 12, and an output driven by the n-type MOSFET 13 in the driving circuit 1.

Moreover, a detailed configuration and a detailed operation of the driving circuit 1 and of the level-shift control circuit 3 are described later.

The further detailed operation and the characteristics of the switch circuit 2 are described later, as well.

<<Driving Circuit 1>>

The driving circuit 1 is configured, comprising the Zener diode 10 (including a case that the breakdown voltage is determined by Zener breakdown and by the avalanche yield of this embodiment), the p-type MOSFET 11 and n-type MOSFETs 12 and 13. The high-voltage positive power supply 5 (VPP) to be a power supply of the driving circuit 1 is connected to an anode terminal of the Zener diode 10 and a cathode terminal of the Zener diode 10 is connected to a source terminal of the p-type MOSFET 11.

Meantime, the high-voltage negative power supply 6 (VNN) to be another power supply of the driving circuit 1 is connected to each of the source terminals of the n-type MOSFETs 12 and 13.

A drain terminal of the p-type MOSFET 11 and a drain terminal of the n-type MOSFET 12 are connected each other, and moreover, output the signal as the first output line 14 of the driving circuit 1.

Furthermore, a drain terminal of the n-type MOSFET 13 outputs a signal as the second output line 15 of the driving circuit 1.

A gate terminal of the p-type MOSFET 11 is connected to the first level-shift control circuit output terminal 18 of the level-shift control circuit 3.

A gate terminal of the n-type MOSFET 13 and a gate terminal of the n-type MOSFET 12 are both connected to the second level-shift control circuit output terminal 19 of the level-shift control circuit 3.

<<Level-Shift Control Circuit 3>>

The level-shift control circuit 3 is a circuit to voltage-transform the signal and to set the signal so as to drive the driving circuit 1 in operation with the high-voltage positive power supply 5 (VPP) and the high-voltage negative power supply 6 (VNN), with the switch control signal 7 (control signal, approximately 0V to 5V). That is to say, the switch control signal, which is between 0V and 5V, is level-shifted (electrical-potential-transformed) into a control signal which is almost equivalent to the voltage VPP or VNN (a voltage difference between VPP and VNN is approximately 200V), at the first level-shift control circuit output terminal 18 and at the second level-shift control circuit output terminal 19 of the level-shift control circuit 3. Therefore, the gates of the p-type MOSFET 11 and the n-type MOSFET 12 are controlled by approximate values of the electrical potentials of VPP and VNN.

Incidentally, the first level-shift control circuit output terminal 18 and the second level-shift control circuit output terminal 19 of the level-shift control circuit 3, may be set into a level of the high-voltage negative power supply 6, simultaneously or with some time difference.

<<Operation of Bi-Directional Analog Switch Overall Circuit 4>>

When the first level-shift control circuit output terminal 18 and the second level-shift control circuit output terminal 19 of the level-shift control circuit 3 are set into an electrical potential level of the high-voltage negative power supply 6 (VNN) by the switch control signal 7, the p-type MOSFET 11 of the driving circuit is switched ON and the n-type MOSFETs 12 and 13 are switched OFF. Accordingly, an electric current flows from the high-voltage positive power supply 5 (VPP)

through the Zener diode 10 and the p-type MOSFET 11, thereafter, gate capacitances at the n-type MOSFETs 16 and 17 of the switch circuit 2 are charged, and subsequently, gate potentials at the n-type MOSFETs 16 and 17 reach an approximate value of the VPP, then consequently, both of the n-type MOSFETs 16 and 17 are switched ON. Accordingly, the switch circuit 2 is switched ON.

When the switch circuit 2 is switched ON and a positive voltage signal is applied to the input/output terminal 8, the voltage of a second output line 15 connected to the source terminals of the n-type MOSFETs 16 and 17 follows a voltage of the input/output terminal 8. This is because the n-type MOSFET 13 is switched OFF and the n-type MOSFET 16 is switched ON.

A voltage between the gate sources of the n-type MOSFETs 16 and 17 is a voltage difference between the first output line 14 and the second output line 15. A first output line 14 in the beginning, that is to say, the gate terminal of the n-type MOSFETs 16 and 17 are in an electrical potential level of the high-voltage positive power supply 5 (VPP) through the driving circuit 1.

As the electrical potential level (voltage) of the positive voltage signal applied to the input/output terminal 8 rises, the voltage of the second output line 15 rises as well, and thereafter, the voltage between the gate sources of the n-type MOSFETs 16 and 17 decreases.

<<Case without Zener Diode 10>>

Here, in order to explain a function of the Zener diode 10 in this embodiment for easy understanding, a case without the Zener diode 10 in the driving circuit 1 is assumed for comparison.

Assuming that the Zener diode 10 does not exist, when a circuit is configured with the p-type MOSFET 11 directly connected to the high-voltage positive power supply 5 (VPP), as a voltage difference between the positive voltage signal applied to the input/output terminal 8 and the voltage of the high-voltage positive power supply 5 (VPP), is getting closer to a threshold voltage of the n-type MOSFETs 16 and 17, an impedance of the n-type MOSFETs 16 and 17 is getting equal to or higher than the initial value. And when the voltage difference reaches the threshold voltage or becomes less than the threshold voltage, the impedance increases drastically.

This is because a boundary between the switch-ON and the switch-OFF of the n-type MOSFETs 16 and 17, as an approximation (a first approximation), is a value to subtract the source electrical potential and the threshold voltage from the gate electrical potential. Furthermore, an impedance of the n-type MOSFETs 16 and 17, is in inverse proportion to the value to subtract the source electrical potential and the threshold voltage from the gate electrical potential, as the approximation (the first approximation).

Accordingly, when a positive voltage signal applied to the input/output terminal 8 is transmitted (propagated) to the input/output terminal 9, each of the input/output terminal 8, source electrical potentials (the second output line 15) of the n-type MOSFETs 16 and 17, and the input/output terminal 9 reaches an electrical potential, which is approximately the same electrical potential as the positive voltage signal applied to the input/output terminal 8.

That is to say, the input/output terminal 8 is not a source (source terminal) of the n-type MOSFETs 16 and 17, however, when a positive voltage signal applied to the input/output terminal 8 is transmitted, an electrical potential of a source (source terminal) of the n-type MOSFETs 16 and 17 needs to be almost the same electrical potential as the positive voltage signal applied to the input/output terminal 8, as well.

Therefore, as the positive voltage signal applied to the input/output terminal 8 is getting higher, and as the voltage difference between the electrical potential of the positive voltage signal and the voltage of the high-voltage positive power supply 5 (VPP) is getting closer to the threshold voltage of the n-type MOSFETs 16 and 17, an impedance of the n-type MOSFETs 16 and 17 is getting higher. Then, a linearity of a signal to be output from the input/output terminal 9, that is to say, a linearity of the switch circuit 2 as a bi-directional analog switch is deteriorated.

<<Case with Zener Diode 10>>

As shown in FIG. 1, a configuration of a circuit connected to the Zener diode 10 in this embodiment, is explained.

Since there exists a parasitic capacitance (not shown) between the gate-sources and that between the gate-drains in the n-type MOSFETs 16 and 17 respectively, as the electrical potential level of the positive voltage signal applied to the input/output terminal 8 rises, the electrical potential level, which is in proportion to the value of the increase of electrical potential level of the positive voltage signal applied to the input/output terminal 8, increases the gate potential of the n-type MOSFETs 16 and 17, due to the parasitic capacitance.

At that moment, in the case of a circuit without the aforementioned Zener diode 10, the gate potential of the n-type MOSFETs 16 and 17 is fixed in a low impedance by the electrical potential VPP of the high-voltage positive power supply, through a first output line 14, the voltage rise to increase the gate potential of the n-type MOSFETs 16 and 17 doesn't make any contribution, due to the aforementioned parasitic capacitance (not shown).

However, as shown in FIG. 1, in the case of a circuit connected with the Zener diode 10 in this embodiment, the electrical potential VPP of the high-voltage positive power supply is not applied directly to the gate of the n-type MOSFETs 16 and 17, thus, the gate potential of the n-type MOSFETs 16 and 17 is increased, by the parasitic capacitance (not shown), to the electrical potential, which is higher than the VPP.

This electrical potential rises, at maximum, up to the voltage which is a sum of the voltage of the high-voltage positive power supply 5 (VPP) and the Zener voltage (breakdown voltage) of the Zener diode 10. Accordingly, even when the electrical potential level of the positive voltage signal applied to the input/output terminal 8 rises, and the voltage difference between the positive voltage signal applied to the input/output terminal 8 and the voltage of the high-voltage positive power supply 5 is equal to or lower than the threshold voltage of the n-type MOSFETs 16 and 17, the electrical potential of a first output line 14, that is to say, the gate terminal of the n-type MOSFETs 16 and 17, rises, at maximum, up to the voltage which is a sum of the voltage of the high-voltage positive power supply 5 (VPP) and the Zener voltage of the Zener diode 10, due to the aforementioned reason. And therefore, in the case of a circuit connected with the Zener diode 10, compared with a circuit not connected with the Zener diode 10, it is possible to prevent a sharp rise of the impedance and to ensure a wider input signal range in which a linearity of the switch circuit 2 can be maintained.

Meanwhile, the reason why the aforementioned electrical potential rises, at maximum, up to the voltage which is a sum of the voltage of the high-voltage positive power supply 5 (VPP) and the Zener voltage of the Zener diode 10, is that a breakdown (avalanche yield) of the Zener diode 10 results in a sudden flow of the electric current, when the electrical potential is equal to or higher than the sum of the voltages.

Furthermore, when the Zener diode 10 is used in a forward direction, a forward direction voltage drop as a diode, is caused. However, in general, the forward direction voltage drop is set sufficiently lower than each of the Zener voltage (breakdown voltage) and the electrical potential VPP of the high-voltage positive power supply, thus the forward direction voltage drop may be negligible.

Due to the aforementioned reason, for example, when the Zener voltage of the Zener diode 10 is identical as the threshold voltage of the n-type MOSFETs 16 and 17, the positive voltage signal applied to the input/output terminal 8 may be applied, at maximum, up to the high-voltage positive power supply 5 (VPP) level.

Moreover, since the Zener diode 10 has the Zener voltage characteristics, when the gate potential of the n-type MOSFETs 16 and 17 is equal to or higher than the sum of the voltage of the high-voltage positive power supply 5 (VPP) and the Zener voltage of the Zener diode 10, the Zener diode 10 breaks down and flows an electric current, as aforementioned. Accordingly, it is prevented that an unnecessarily high voltage of an element device inside the driving circuit 1 or the switch circuit 2 causes an insulation breakdown of the element device itself or vicinities thereof.

Incidentally, the above mentioned case is that the positive voltage signal is applied to the input/output terminal 8 and propagated (transmitted) to the input/output terminal 9. The similar effect and characteristics are caused, in case that the positive voltage signal is applied to the input/output terminal 9 and propagated (transmitted) to the input/output terminal 8, since the switch circuit 2 is of a symmetrical configuration.

Moreover, when a negative voltage signal is applied to the input/output terminal 8, the value to subtract the source electrical potential and the threshold voltage from the gate electrical potential of the n-type MOSFET 16 is a positive value, which is sufficiently higher than zero. Thus, the n-type MOSFETs 16 and 17 propagate (transmit) a negative voltage signal to the input/output terminal 9, under a condition of a low impedance with little variation, that is to say, under a condition of a high linearity.

Furthermore, when a negative voltage signal is applied to the input/output terminal 9, the switch circuit 2, because of a symmetrical configuration, propagates (transmits) a negative voltage signal to the input/output terminal 8, under a condition of a low impedance with a small variation, that is to say, under a condition of a high linearity.

As a consequence, a bi-directional analog switch is realized, having a high linearity to an AC signal which is an alternating positive and negative signal and moreover to an AC signal of a large amplitude, by having a high linearity to both of the positive voltage signal and the negative voltage signal.

Incidentally, the measured values of the different impedance characteristics in case with the Zener diode 10 and in case without the Zener diode 10, is described in detail later.

<<Low Electric Power Loss>>

In order to switch OFF the switch circuit 2, a first level-shift control circuit output terminal 18 and an electrical potential level of a second level-shift control circuit output terminal 19 of a level-shift control circuit 3 are set to an electrical potential level of a high-voltage positive power supply 5. By setting the first level-shift control circuit output terminal 18 and the second level-shift control circuit output terminal 19 to the electrical potential level of the high-voltage positive power supply 5 (VPP), the p-type MOSFET 11 of the driving circuit is switched OFF, and the n-type MOSFETs 12 and 13 of the driving circuit are switched ON. Accordingly, a gate capacitance of the n-type MOSFETs 16 and 17 of the switch circuit 2 is discharged and the switch circuit 2 is switched OFF.

When this switch circuit 2 is switched OFF, the p-type MOSFET 11 is switched OFF, and moreover, there is no other path to flow an electric current. Thus, no any electric current flows in a stationary manner between the high-voltage positive power supply 5 (VPP) and the high-voltage negative power supply 6 (VNN). Accordingly, the electric power loss is decreased compared to a comparison circuit which is described later as a reference.

Incidentally, the electrical potential levels, of a first level-shift control circuit output terminal 18 and of a second level-shift control circuit output terminal 19 of the level-shift control circuit 3, may be set into an electrical potential level of the high-voltage positive power supply 5 (VPP), simultaneously or with some time difference.

Second Embodiment

Semiconductor Device

Figure 2:
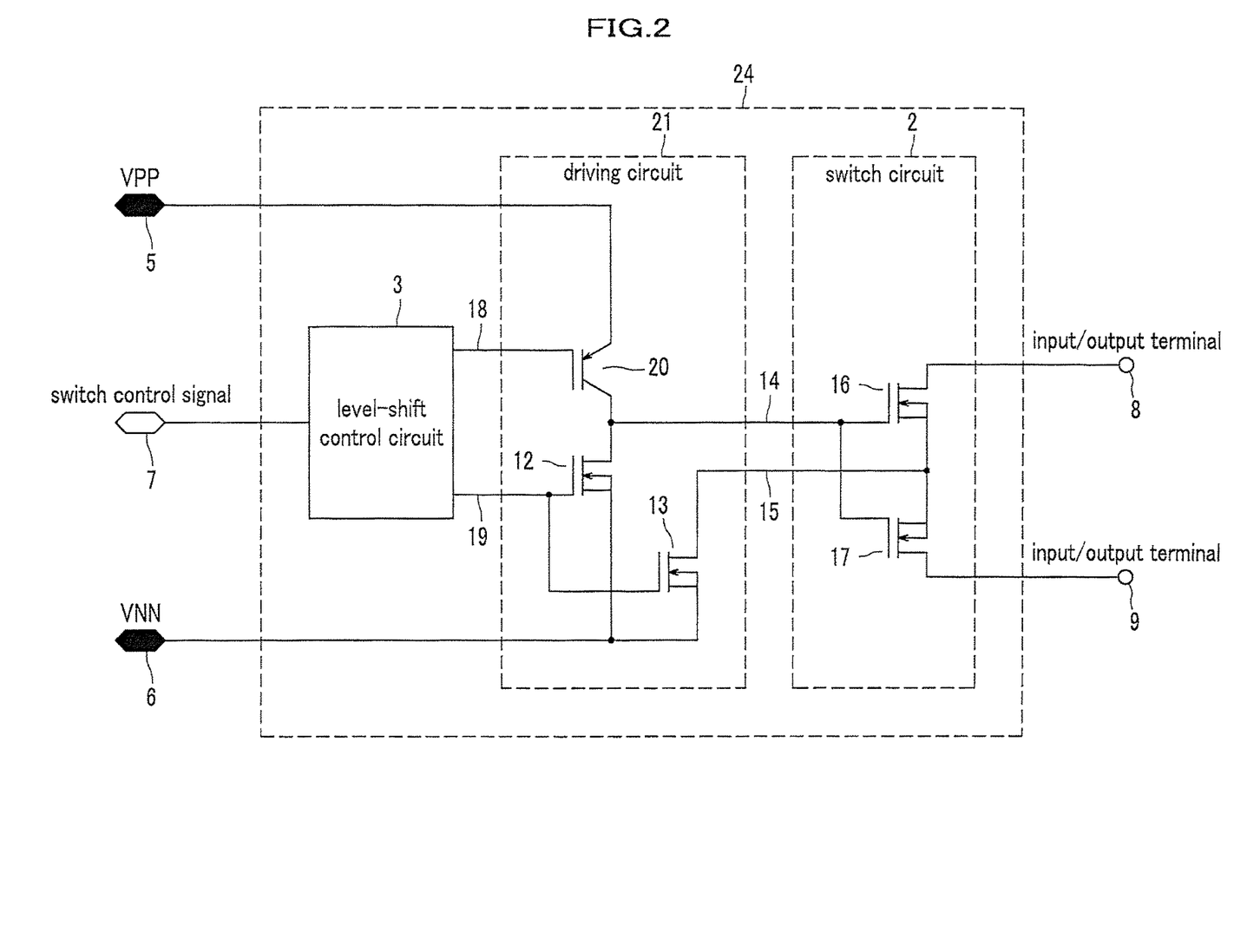
FIG. 2 is a circuit diagram showing a configuration of a semiconductor device according to a second embodiment of the present invention.

FIG. 2 is a circuit diagram showing a second embodiment of the present invention. In FIG. 2, a semiconductor device in the second embodiment comprises a bi-directional analog switch overall circuit 24.

In FIG. 2 of a driving circuit 21, comprised in the bi-directional analog switch overall circuit 24, the Zener diode 10 and a p-type MOSFET 11 of a driving circuit 1 in FIG. 1 are substituted with the p-type IGBT (Insulated Gate Bipolar Transistor) 20. This p-type IGBT, as described later, has a structure to comprise the built-in Zener diode, and therefore, the p-type IGBT may be substituted with the Zener diode 10 and the p-type MOSFET 11 in FIG. 1, accordingly.

In FIG. 2, the Zener diode 34 (FIG. 3) which is built in to the p-type IGBT 20, has an inverted withstand voltage corresponding to the Zener voltage in a switch-ON state. Accordingly, a configuration comprising the p-type IGBT 20 to switch ON and OFF the high-voltage positive power supply 5 (VPP) and the Zener diode 34 (FIG. 3) built in the p-type IGBT 20, has a function and an effect, which are approximately equivalent to a function and an effect of a configuration comprising the p-type MOSFET 11 and a Zener diode 10 in FIG. 1. Therefore, the p-type IGBT 20 ensures a wider input signal range in which a switch circuit 2 is capable of maintaining a linearity.

Figure 3:
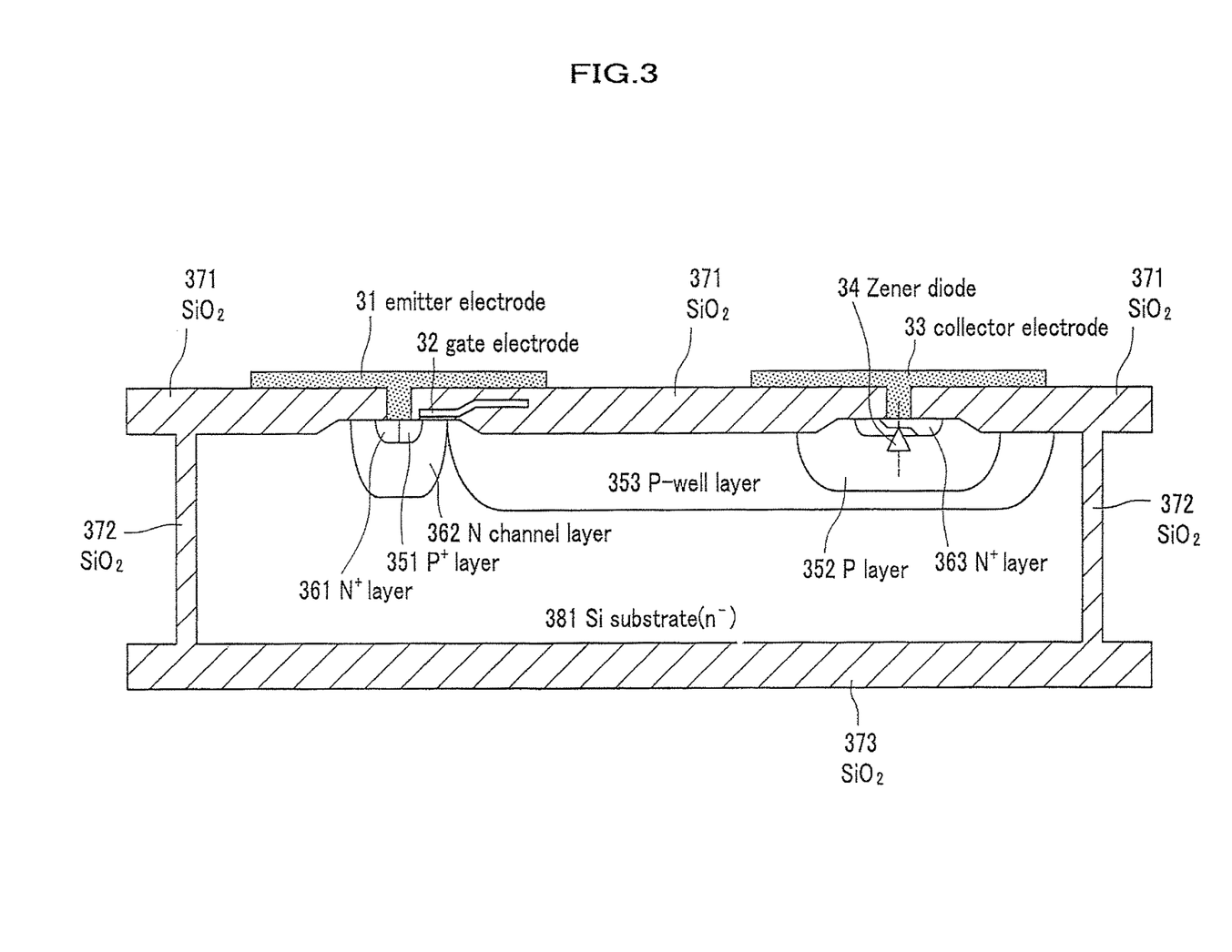
FIG. 3 is a sectional view showing a structure of a p-type IGBT comprised by a semiconductor device according to a second embodiment of the present invention.

Incidentally, the Zener diode 34 (FIG. 3) which is built in to the p-type IGBT 20, as described later, is formed in a side of the collector electrode 33 (FIG. 3). That is to say, in FIG. 2, the Zener diode is formed in a side of a first output line 14. However, an effect as a Zener diode is the same as the effect in FIG. 1, even if the Zener diode is not located in a side of the high-voltage positive power supply VPP. Thus, an electrical potential of a first output line 14 can maintain a value to add the Zener voltage to the voltage of the high-voltage positive power supply (VPP), resulting in a effect to ensure a wider input signal range in which the switch circuit 2 can maintain a linearity, as aforementioned.

Furthermore, since configurations other than the p-type IGBT 20 are the same as the configurations in FIG. 1, redundant description thereof will be omitted.

<<p-Type IGBT Structure>>

FIG. 3 is a sectional view showing a structure of a p-type IGBT.

In FIG. 3, an emitter electrode 31 is connected to a $P^+$ layer 351. An N channel layer 362 lies between the $P^+$ layer 351 and a P-well layer 353. By controlling switch-ON and switch-OFF with a gate electrode 32, this part of the structure configures a MOSFET. The structure comprises the aforementioned P-well layer 353, furthermore, a P layer 352, an $N^+$ layer 363 (this part is a bipolar structure), and a collector electrode 33, connected. A major part of the IGBT is configured as above.

In addition, in FIG. 3, each of an $N^+$ layer 361, an Si substrate (n−) 381, an $SiO_2$ (layer) 371, 372 and 373 is a structurally necessary element to configure IGBT as a device.

In the configuration above, a diode 34 is configured by the $N^+$ layer 363 and the P layer 352, directly under the collector electrode 33. Here, by an appropriate selection of an impurity density of the P layer 352 or the $N^+$ layer 363, it is possible to make a diode configured by an $N^+$ layer 363 and the P layer 352, into the Zener diode 34. The Zener diode 34 configured by the $N^+$ layer 363 and the P layer 352 gives, in a driving circuit 21 of FIG. 2, the same effect as the Zener diode 10 in FIG. 1.

Furthermore, a process to manufacture a p-type IGBT as a device, comprises a plurality of processes to configure the P layer, and therefore, by applying an existing ion implantation process or a diffusion process for an appropriate impurity density into the P layer 352 to configure the aforementioned the Zener diode 34, it is possible to form the aforementioned Zener diode 34, without adding a new manufacturing process, that is to say, without any cost increase.

<<Impedance Characteristics>>

Figure 4:
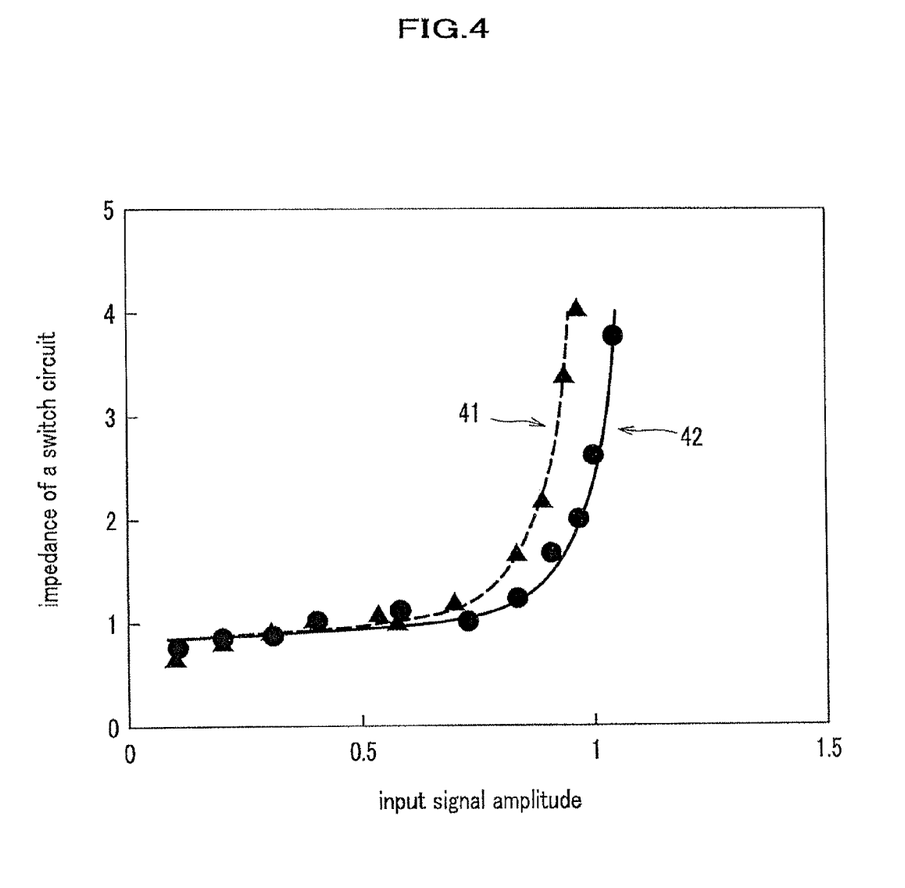
FIG. 4 is a schematic diagram showing a relation graph between an input signal amplitude and an impedance between input and output terminals of a switch circuit, of a semiconductor device of the present invention.

FIG. 4 shows a measurement result of an impedance of the switch circuit 2 (FIG. 1) against an input signal amplitude of a circuit in FIG. 1, and is a characteristics diagram to compare the impedance characteristics in cases with and without the Zener diode 10.

In FIG. 4, a horizontal axis shows a normalized input signal amplitude, and a reference value is set as 1, under a condition that an input signal amplitude is equal to a VPP voltage of the high-voltage positive power supply.

Furthermore, a vertical axis shows a normalized value of an impedance of a switch circuit 2, and a reference value is set as 1 for an impedance value under a condition that an input signal amplitude is equal to 0.5 (a half of the VPP voltage).

In FIG. 4, a region showing almost a flat impedance of a switch circuit 2 (FIG. 1) is a range where a linearity is maintained. A characteristics line 41 is a measurement result of the circuit not connected with the Zener diode 10 (FIG. 1), and meantime, a characteristics line 42 is a measurement result of the circuit connected with the Zener diode 10. By connecting the Zener diode 10, a dynamic range of an input signal amplitude becomes wider and a linear domain is extended. In the domain showing a drastic increase of an impedance of the characteristics line 41 and the characteristics line 42, the difference between the characteristics line 41 and the characteristics line 42 along the horizontal axis direction, corresponds almost to the Zener voltage of the Zener diode 10 (FIG. 1). Incidentally, as aforementioned, FIG. 4 shows a measurement result of the circuit in FIG. 1, and furthermore, in case that an IGBT 20 of FIG. 2 is utilized, the built-in Zener diode 34 (FIG. 3) causes almost the same characteristics improvement.

Third Embodiment

Ultrasonic Diagnostic Apparatus

Next, an ultrasonic diagnostic apparatus of a third embodiment of the present invention is explained with reference to FIG. 5 and FIG. 6.

Figure 5:
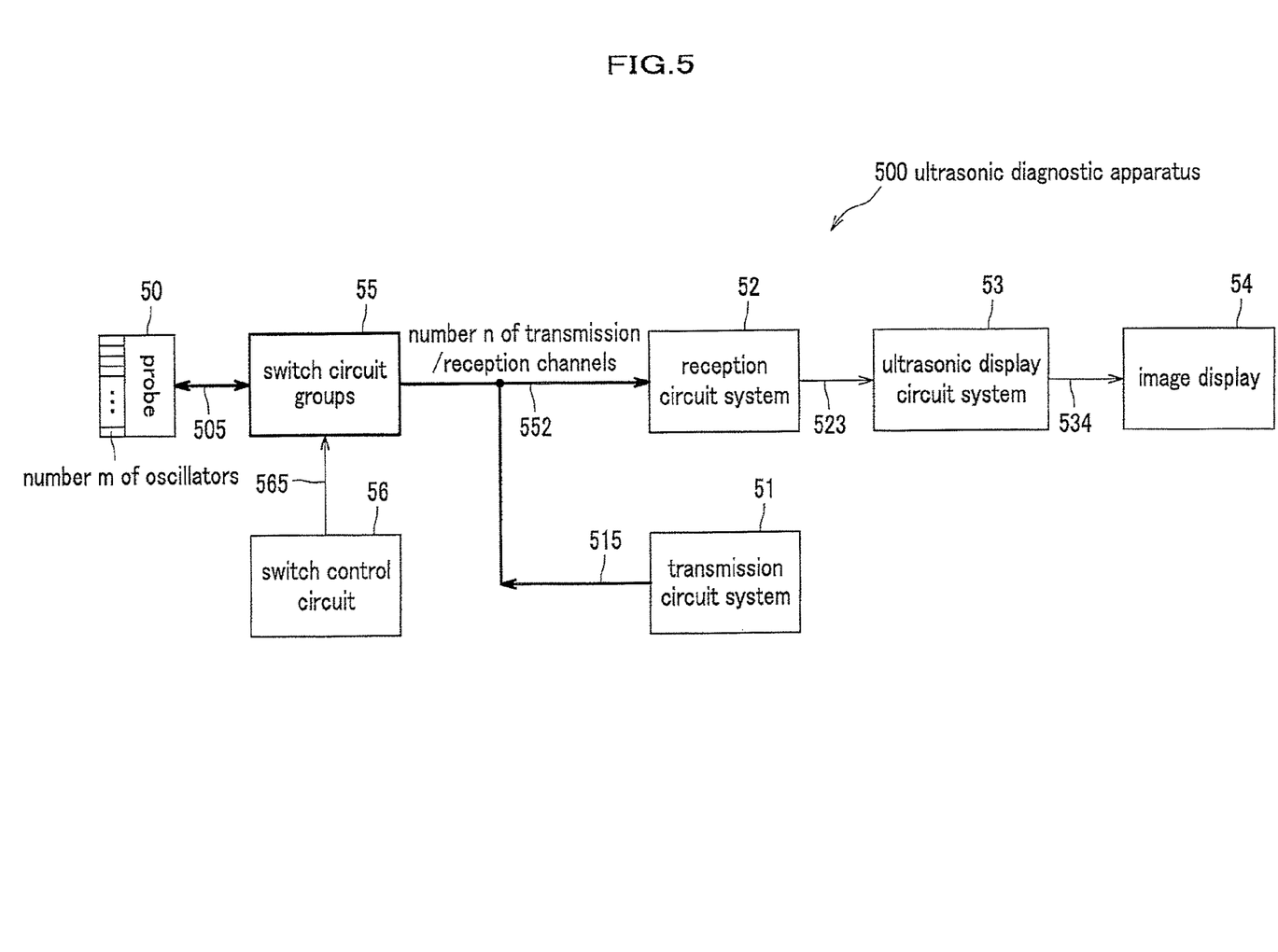
FIG. 5 is a block diagram showing a functionality structure of an ultrasonic diagnostic apparatus utilizing a semiconductor device according to a third embodiment of the present invention.

FIG. 5 is a block diagram showing a functionality structure of an ultrasonic diagnostic apparatus 500 of a third embodiment of the present invention, comprising a semiconductor device according to the first embodiment or the second embodiment of the present invention.

In FIG. 5, the ultrasonic diagnostic apparatus 500 comprises; an ultrasonic probe 50 for transmitting and receiving an ultrasonic to and from an internal part of an examinee (not shown) to be measured, a transmission circuit system means 51 for transmission-focus-processing a transmission wave to the ultrasonic probe 50 and transmitting an ultrasonic, a reception circuit system means 52 comprising a phasing means for reception-focus-processing a reception wave output from the ultrasonic probe 50, and switch circuit groups 55 for switching an ultrasonic signal transmitted among the ultrasonic probe 50, and the transmission circuit system means 51, and the reception circuit system means 52.

In addition, the ultrasonic diagnostic apparatus 500 further comprises; an ultrasonic display circuit system means 53 for displaying an ultrasonic tomography image or the like using a reception signal output from the reception circuit system means 52, and an image display 54, for example, a monitor display or the like, for displaying an ultrasonic image information output from the ultrasonic display circuit system means 53.

Furthermore, signal lines 505, 515, and 552 in bold lines show an ultrasonic transmission/reception signal flow, and signal lines 523, 534, and 565 in fine lines show a control signal flow.

Meanwhile, in FIG. 5, the ultrasonic probe 50, the transmission circuit system means 51, the reception circuit system means 52, and the ultrasonic display circuit system means 53 are referred to as "probe", "transmission circuit system", "reception circuit system", and "ultrasonic display circuit system", respectively, for the simplification in the block diagram.

The ultrasonic diagnostic apparatus 500 of this embodiment comprises a semiconductor device, of the aforementioned embodiment, utilized for the switch circuit groups 55 for switching an ultrasonic signal transmitted among a number m of oscillators equipped in the ultrasonic probe 50 and the transmission circuit system means 51, and the reception circuit system means 52.

The switch circuit groups 55 are provided among the transmission circuit system means 51, and the reception circuit system means 52, and the ultrasonic probe 50. Incidentally, a number n of the transmission/reception channels are connected between the switch circuit groups 55 and the transmission circuit system means 51, and between the switch circuit groups 55 and the reception circuit system means 52.

Figure 6:
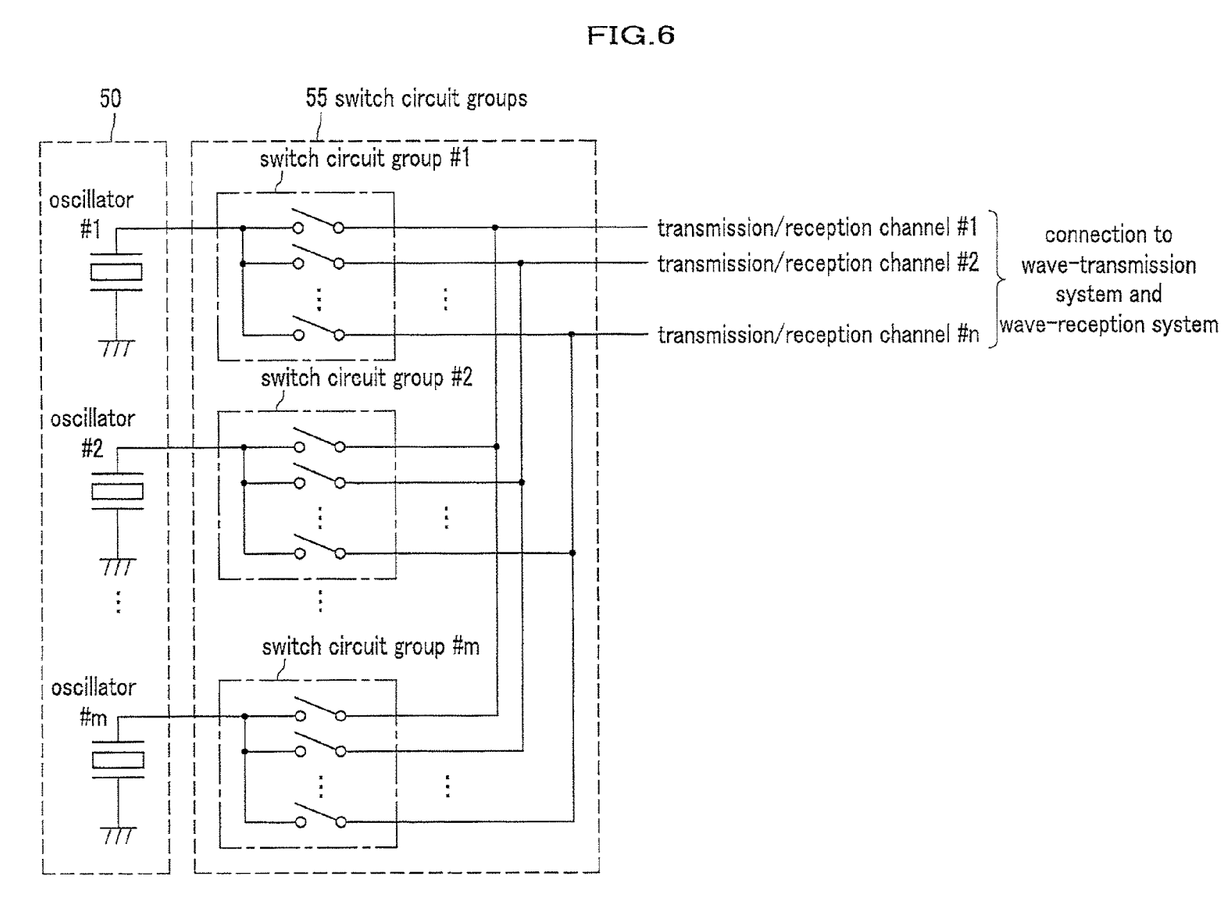
FIG. 6 is a circuit diagram showing a partial and detailed configuration of an ultrasonic diagnostic apparatus utilizing a semiconductor device according to a third embodiment of the present invention.

The configuration of the switch circuit groups 55 in FIG. 5 is exemplified in the switch circuit groups 55 in FIG. 6, in more detail.

In FIG. 6, the switch circuit groups 55 consist of a number m of switch circuit groups, that is to say, a switch circuit group #1 through #m, each of which comprises a number n of the switches (semiconductor devices 4 (FIG. 1) and 24 (FIG. 2)). One terminal of the number n of the switches (semiconductor devices 4 (FIG. 1) and 24 (FIG. 2) comprised in each switch circuit group is connected to each other and to an oscillator comprised in the ultrasonic probe 50. That is to say, each of the commonly-connected terminals in each of the switch circuit group #1 through #m is connected to the one terminal of the oscillator #1 through #m comprised in the ultrasonic probe 50. Furthermore, the other terminals of the oscillator #1 through #m are earthed (grounded).

Moreover, each of other terminals of a number n of switches (semiconductor devices 4 (FIG. 1) and 24 (FIG. 2) comprised in each of the switch circuit groups is connected to the transmission/reception channel #1 through #n. Incidentally, each of the number m of the oscillators comprised in the ultrasonic probe 50 in FIG. 5 corresponds to each of the oscillator #1 through #m in FIG. 6.

Meanwhile, each of the number n of the transmission/reception channel 515 and 552 in FIG. 5 corresponds to each of the transmission/reception channel #1 through #n in FIG. 6.

Furthermore, the switch control circuit 56 (FIG. 5) selects and controls the switch circuit group (#1 through #m) of the switch circuit groups 55 and a number n of switches (semiconductor devices 4 (FIG. 1) and 24 (FIG. 2) comprised in each thereof, by the control signal 565 (FIG. 5).

In the aforementioned configuration, the transmission circuit system means 51 applies a voltage of an approximately one hundred and several dozens of volts to the oscillator #1 through #m and the oscillator transmits an ultrasonic beam to an internal part of an examinee (not shown) to be measured. Meanwhile, after the pre-determined time passes, a reflection wave is detected by the oscillator #1 through #m, furthermore, the transformed electric signal (approximately several dozens of milli-volts) is transmitted to the reception circuit system means 52, thereafter, the signal processing is performed.

In the processes above, each of the switch circuit group (#1 through #m) in the switch circuit groups 55 selects one out of a plurality of ultrasonic transmission/reception channels for a plurality of oscillators (#1 through #m) to transmit and to receive an ultrasonic in an ultrasonic probe, otherwise shuts down all transmission/reception channels.

Furthermore, when the oscillator (#1 through #m) transmits an ultrasonic beam, the switches (semiconductor devices 4 (FIG. 1) and 24 (FIG. 2)) need to have high blocking voltage characteristics, since an aforementioned high voltage is applied to the switch. Moreover, since a high degree of detection accuracy is required to transmit and to receive an ultrasonic, the switches (semiconductor devices 4 (FIG. 1) and 24 (FIG. 2)) need a high linearity and a wide dynamic range.

An ultrasonic diagnostic apparatus 500 in this embodiment is capable of driving a large amplitude of an ultrasonic signal, by utilizing a semiconductor device in this aforementioned embodiment for a switching apparatus of the ultrasonic signal transmitted among the oscillators, the transmission circuit system, and the reception circuit system. This improves the S/N ratio (signal-to-noise ratio) of the ultrasonic signal and can improve the image quality of the ultrasonic diagnostic apparatus.

Other Embodiment

In FIG. 1, the Zener diode 10 is comprised between the p-type MOSFET 11 and a high-voltage positive power supply 5 (VPP), meanwhile, the Zener diode 10 may be comprised between the p-type MOSFET 11 and the first output line 14. In either case that the Zener diode 10 is comprised in a side of the source or in a side of the drain of the p-type MOSFET 11, the first output line 14 has an effect to maintain a value to add the Zener voltage of the Zener diode 10 to an electrical potential of the voltage of the high-voltage positive power supply (VPP).

Furthermore, the Zener diode 10 may be formed in the same manufacturing process (common manufacturing process) as the p-type MOSFET 11 and within the same substrate as the p-type MOSFET 11. In the manufacturing process of the p-type MOSFET 11, both of P layer and N layer are manufactured therein. Accordingly, it is possible to manufacture a Zener diode consisting of P layer and N layer within the same substrate as the p-type MOSFET, and furthermore, in the different insulation-isolated domain ($SiO_2$ layer). Moreover, it is also possible to adjust the Zener voltage characteristics by ion-implanting an impurity into P layer or N layer of the Zener diode.

In addition, the Zener diode 10 may be formed in the same manufacturing process (common manufacturing process), and within the same substrate as the p-type MOSFET 11, n-type MOSFETs 12, 13, 16 and 17, and the level-shift control circuit 3.

In the manufacturing process of CMOS (Complementary Metal Oxide Semiconductor), since the p-type MOSFET and the n-type MOSFET are formed in the same manufacturing process (common manufacturing process), and within the same substrate, it is further possible to manufacture a Zener diode which consists of P layer and N layer. Manufacturing the Zener diode 10 and each of the aforementioned element devices in the same manufacturing process (common manufacturing process) and within the same substrate, results in the further cost reduction.

Furthermore, in FIG. 2, an explanation is made about a case to utilize an IGBT having a built-in Zener diode. Meanwhile, when any specific performance such as an accuracy is required in Zener voltage characteristics of the Zener diode, IGBT and the Zener diode may be configured in separate components.

Moreover, in FIG. 1 and FIG. 2, a MOSFET to configure the switch circuit 2, is explained by the n-type MOSFET. Meanwhile, the p-type MOSFET may configure the switch circuit 2. In this case, however, the configuration of the driving circuit 1 or 21, and the level-shift control circuit 3 should be modified so as to correspond to a polarity of the p-type MOSFET.

In addition, in FIG. 1 and FIG. 2, the p-type MOSFET may be added in parallel to each of n-type MOSFETs 16 and 17 to configure the switch circuit 2. In this case, however, the configuration of the driving circuits 1 (FIG. 1) and 21 (FIG. 2), and the level-shift control circuit 3 should be modified so as to include a circuit to drive the added p-type MOSFET.

Furthermore, in FIG. 5 and FIG. 6, an explanation is made about a case to utilize a semiconductor device of the first embodiment or the second embodiment of the present invention for switching the transmission/reception of the ultrasonic signal to the oscillator in the ultrasonic diagnostic apparatus (a switch for separating the wave-transmission pulse generator and the reception amplifier of the ultrasonic signal). However, the semiconductor device may be utilized for switching the transmission, only.

Moreover, the semiconductor device of this embodiment may be utilized for switching a probe in the ultrasonic diagnostic apparatus.

Comparable Circuit Technology for Reference

Figure 7:
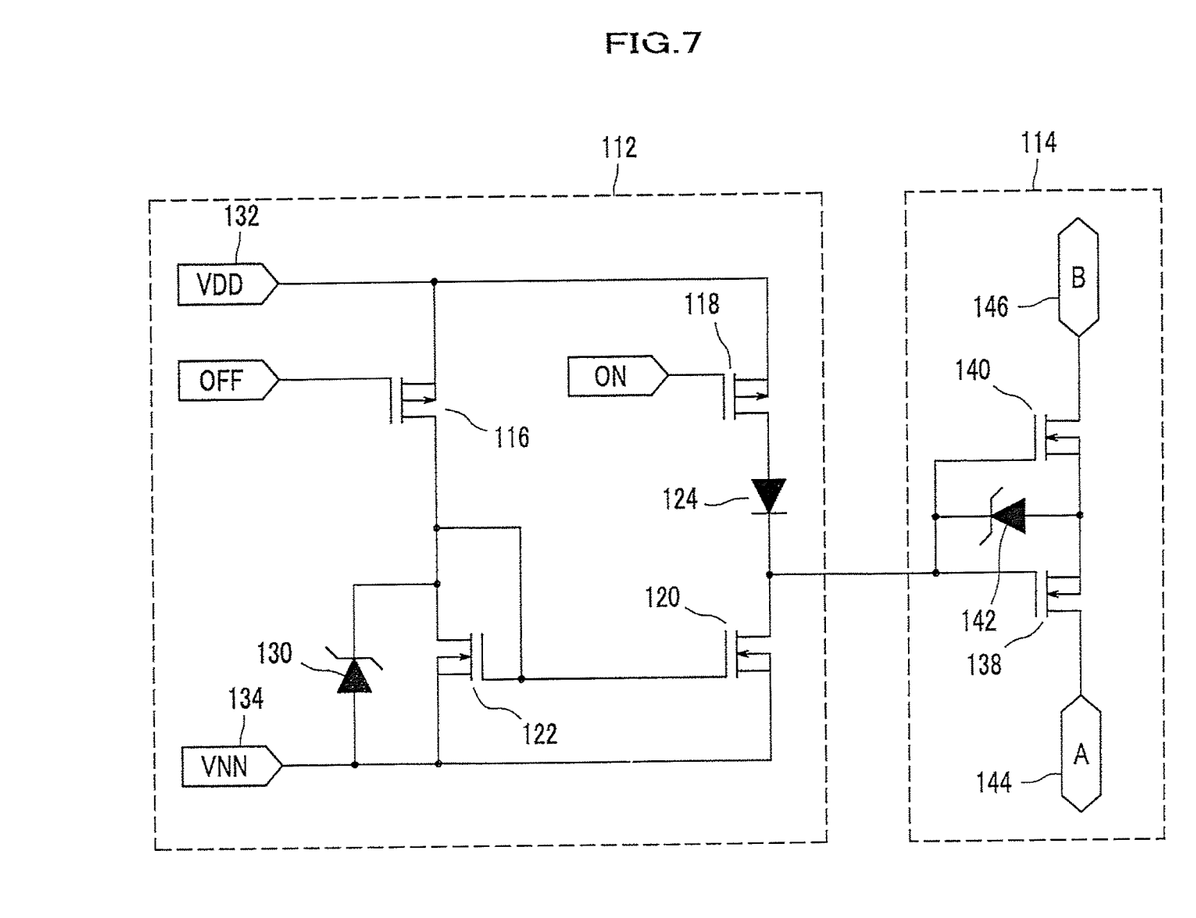
FIG. 7 is a circuit diagram showing a configuration of a bi-directional analog switch circuit and a driving circuit thereof of a circuitry technology referred to for comparison.

As a comparable circuit technology for reference, a configuration of the bi-directional analog switch circuit and the driving circuit thereof, is shown in FIG. 7. FIG. 7 shows an example to configure a bi-directional analog switch. In FIG. 7, the bi-directional analog switch 114 comprising of the transistors 140 and 138 and a Zener diode 142, is controlled by the level-shifter 112 comprising the transistors 116, 118, 120 and 122, the diode 124 and the Zener diode 130.

This configuration provides a device to widen a dynamic range so as to maintain a linearity as a bi-directional analog switch 114.

However, when the bi-directional analog switch 114 is in a switch-ON state and applies a negative voltage signal to the switch terminal 144, an electric current flows from the power supply 132, through the transistor 118, the diode 124 and the Zener diode 142. Accordingly, all of the electric currents in the level-shifter 112 flow outward from either of the switch terminal 144 or the switch terminal 146.

Moreover, when the bi-directional analog switch 114 is in a switch-OFF state, an electric current flows between the power supplies 132 and 134 through the transistors 116 and 122, and the Zener diode 130.

Accordingly, in either case that the bi-directional analog switch 114 is in switch-ON state or in switch-OFF state, an electric current continues flowing as a leak electric current in the level-shifter 112 which is a control circuit. That is to say, the comparison circuit exemplified in FIG. 7 for reference, causes a larger electric power loss.

To the contrary, in the case of a semiconductor device which is a bi-directional analog switch of this aforementioned embodiment, there is no path to flow a leak electric current which flows in the comparison circuit mentioned above, and therefore, an electric power loss is reduced.

Supplementary Information of this Embodiment

As aforementioned in this embodiment, by utilizing the p-type MOSFET and the Zener diode connected in series, or by connecting the p-type IGBT with the built-in Zener diode, a voltage between a gate and a source of the n-type MOSFET in the switch circuit keeps equal to or higher than the Zener voltage within the operation condition of the switch circuit. Therefore, the aforementioned switch circuit achieves a high linearity as a bi-directional analog switch.

Furthermore, while the switch circuit keeps a switch-ON state or a switch-OFF state, an insulation is made between the power supplies. Therefore, no leak electric current flows and it is possible to reduce an electric power loss, compared with the prior art. In addition, all or a part of the driving circuits 1 and 21 including the Zener diode, the switch circuit 2, and a level-shift control circuit 3, are formed in the same manufacturing process (common manufacturing process) and within the same substrate device, into a semiconductor device, and therefore, a cost reduction would be achieved.

Moreover, by comprising the aforementioned semiconductor device as a bi-directional analog switch, an improvement of a high degree of detection accuracy of the ultrasonic diagnostic apparatus is expected.

A bi-directional analog switch, especially a high-voltage bi-directional analog switch, is utilized firstly in the medical field, and also extensively in an entirety of various industries. A high-voltage bi-directional analog switch utilizing a semiconductor device according to this embodiment of the present invention, is feasibly to be used not only in a medical field, but also extensively in a field of analog signal switches utilizing a semiconductor for industrial use and for home use, because of a high linearity in the analog characteristics and a low electric power loss suitable for the miniaturization use and the mobility use, and furthermore, because of the low cost.

What is claimed is:

1. A semiconductor device comprising:
   a switch circuit capable of switching ON or switching OFF, bi-directionally; and
   a driving circuit for driving the switch circuit,
   wherein,
      the driving circuit is connected to a first power supply comprising a first power supply voltage which is equal to or higher than a maximum voltage of a signal applied to a first terminal comprising an input or output terminal of the switch circuit, and the driving circuit is connected to a second power supply comprising a second power supply voltage which is equal to or lower than a minimum voltage of a signal applied to a second terminal comprising an input or output terminal of the switch circuit; and
      the driving circuit comprises a Zener diode and a p-type MOSFET connected in series between the first power supply and the switch circuit.

2. A semiconductor device as claimed in claim 1, further comprising a level-shift control circuit for level-shifting a switch control signal to control the driving circuit.

3. A semiconductor device as claimed in claim 2, wherein the driving circuit comprising the Zener diode and the p-type MOSFET, the switch circuit, and the level-shift control circuit are formed in a common manufacturing process and within a same substrate.

4. A semiconductor device as claimed in claim 1, wherein a Zener voltage of the Zener diode is equal to or higher than a threshold voltage of an n-type MOSFET of the switch circuit.

5. A semiconductor device as claimed in claim 1, wherein the switch circuit is a bi-directional analog switch circuit for
   connecting source terminals of two of n-type MOSFETs each other; and
   connecting gate terminals of two of n-type MOSFETs each other.

6. An ultrasonic diagnostic apparatus, wherein the semiconductor device as claimed in claim 1 is utilized for
   switching a wave-transmission of an ultrasonic signal to an oscillator,
   separation-switching a wave-transmission pulse generator and a reception amplifier of the ultrasonic signal; or
   switching a probe.

\* \* \* \* \*